United States Patent [19]
Garbe

[11] Patent Number: 5,722,417
[45] Date of Patent: Mar. 3, 1998

[54] LONG FUNCTION MONITORING APPARATUS FLOWHEADS

[76] Inventor: Bernhardt Rudolph Garbe, Green Acres, Thrornborough, Buckinghamshire MK18 2DJ, United Kingdom

[21] Appl. No.: 672,541
[22] Filed: Jun. 28, 1996

[30]  Foreign Application Priority Data

Jun. 30, 1919 [GB] United Kingdom ............... 9513370.8

[51] Int. Cl.[6] ............................................. A61B 5/087
[52] U.S. Cl. ......................... 128/725; 128/716; 73/861.52
[58] Field of Search ............................ 128/716, 720, 128/724, 725; 73/861.52

[56]  References Cited

U.S. PATENT DOCUMENTS

| | | | |
|---|---|---|---|
| 5,060,655 | 10/1991 | Rudolph | 128/725 |
| 5,107,860 | 4/1992 | Malouvire et al. | |
| 5,357,972 | 10/1994 | Norlien | |
| 5,564,432 | 10/1996 | Thomson | 128/725 |

FOREIGN PATENT DOCUMENTS

EP 0 627 196 A1 12/1994 European Pat. Off..

Primary Examiner—Jennifer Bahr
Assistant Examiner—Rosiland Kearney
Attorney, Agent, or Firm—Breiner & Breiner

[57]  ABSTRACT

Flowheads are described for use in expiratory flow measuring equipment. They are designed to be disposable and to fit on the casing of a unit containing a pressure transducer and associated electronics. The pressure transducer is placed, when the unit is fitted to the casing, in communication with ports (8 and 9) in the wall of a main tube, which ports are respectively upstream and downstream of a central perforated wall (5) which constitutes a passage restriction and across which a pressure drop is accordingly generated if breath is exhaled through the tube. Low pressure drop hydrophilic filters may be used to damp high frequency pressure oscillations and to protect the instrument from ingress of condensed water vapour.

2 Claims, 1 Drawing Sheet

LONG FUNCTION MONITORING APPARATUS FLOWHEADS

FIELD OF THE INVENTION

This invention relates to lung function monitoring apparatus.

BACKGROUND OF THE INVENTION

In various diagnostic and monitoring procedures for people with breathing difficulties, particularly asthmatics, it is desirable to be able to carry out checking on a number of physiological parameters. Two of the most important of these for diagnostic purposes is the peak expiratory flow i.e. the maximum flow rate at which the person can exhale, and the $FEV_1$ (Forced Expiratory Volume at one second), that is the volume expired in the first second.

Simple mechanically operating peak flow meters have been known for some time and have acquired widespread popularity. They are inexpensive to manufacture and can be issued to individual patients for continuous monitoring, for example checking their peak expiratory flow three times a day. Devices of this type are described for example in patent specifications GB 1463814 and WO 91/11140.

For more sophisticated and accurate testing and measurements, spirometers are available. These generally cost hundreds or thousands of pounds and are widely used in clinical practice, but they are not suitable for quick checking, they are not particularly portable, and accordingly not always convenient for use.

With the advent of modern electronics, it is possible to produce considerably more compact apparatus which may be used by medical professionals and even be designed for personal use. UK-A-2238389 describes such apparatus. The apparatus described in that specification, however, is effectively restricted to personal use by a single user since it will naturally, even if mouth pieces with filters are used, be subject to bacterial contamination from the users exhaled breath and thus cannot be used by another patient without danger and cross infection.

A classic approach to measuring fluid flow is to cause the fluid flow to pass through a channel containing a constriction and measuring the pressure in the channel upstream and downstream of the constriction. Nowadays electronic differential pressure transducers are widely available and one of these e.g. located at the ends of a pair of lateral channels one upstream and one downstream of the constriction in the flow passage, can be connected to suitable circuitry to analyze and display the result. The present invention is directed to the construction of a channel member through which the exhaled air is expelled, and which can be produced inexpensively as a disposable unit which can be easily attached to, and detached from, a basic electronic measuring unit containing the transducer and associated circuitry. A particular advantage of the present invention is that the disposable flowheads may be manufactured in a very consistent manner so as to have a constant differential pressure across the flowhead which has the result that the electronic measuring unit does not lose calibration when the flowhead is changed.

GENERAL DESCRIPTION OF INVENTION

According to the present invention there is provided a flowhead for use in such apparatus consisting of a body member defining a substantially cylindrical main channel divided transversely into two sections via a mesh extending across the entire cross-section of the channel, axially spaced ports in the side wall of the channel to either side of the mesh, the axis of each port being transverse to the longitudinal axis of the channel and parallel the axes of the ports being with one another, and wherein each port is surrounded on the exterior of the channel by a cylindrical sealing collar.

The sealing collars are designed to mate with corresponding cylindrical sleeves or apertures on the casing containing the transducers and associated electronics, each sleeve or aperture surrounding a passage leading to a transducer.

The mesh dividing the channel is preferably an integrally moulded mesh consisting of a series of narrow generally cylindrical passages axially aligned with the main axis of the channel. Alternatively the mesh may be inserted into the moulding, the moulding could take place around a preformed mesh; or the moulding could take place around a piece of material which is to be machined into a mesh at a later time in the manufacturing process.

It is highly preferred to incorporate within the passages on either side of the mesh and covering the lateral ports a hydrophilic filter material, preferably one based on a non-woven fabric such as those commercially available under the trade mark FILTRETE. The use of such filter material assists in damping out high frequency pressure oscillations and according reducing the possibility of damage to the pressure transducers.

The mesh design not only creates a pressure drop between the two ports of the channel but is also preferably designed to ensure a consistently turbulent flow profile across the entire cross-section of the channel.

DESCRIPTION OF PREFERRED EMBODIMENT

Figure 1:
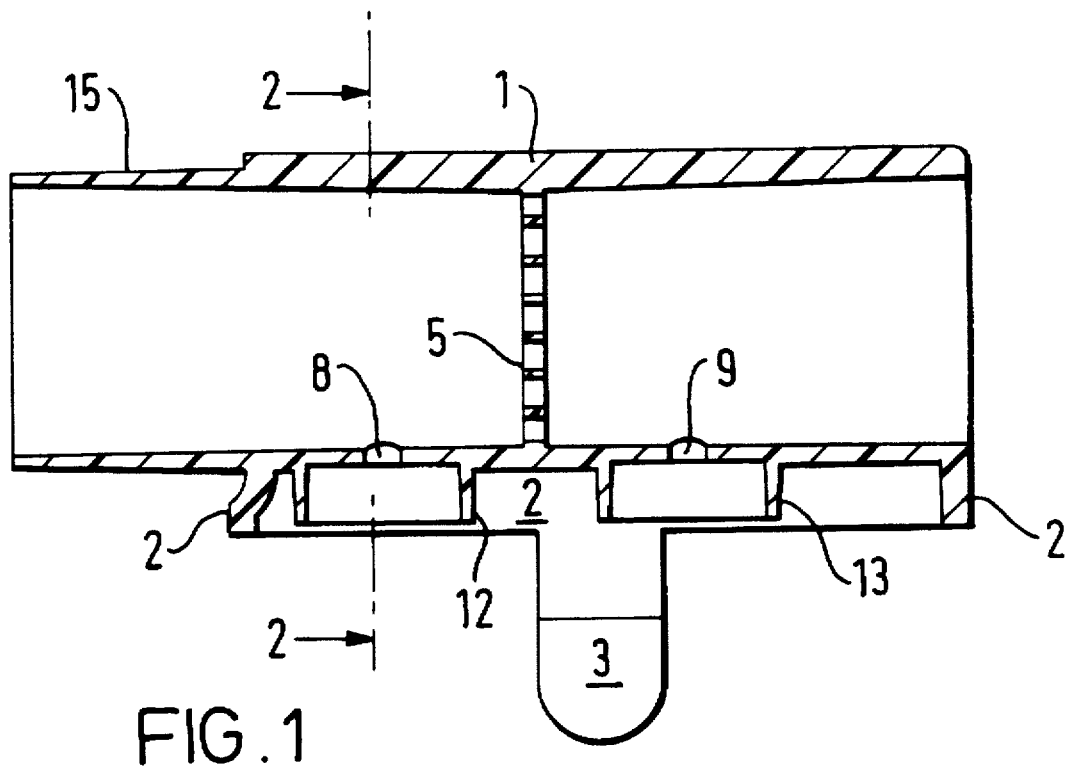
Figure 2:
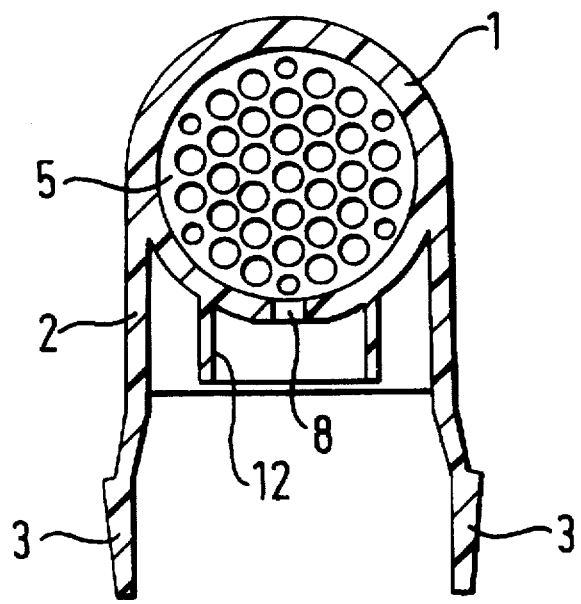

The invention is illustrated by way of example with reference to the accompanying drawings in which:

FIG. 1 is an axial section through a disposable flowhead in accordance with the invention, and FIG. 2 is a cross-section along the lines 2—2 in FIG. 1.

Referring to the drawings, the unit consists basically of a main tubular body 1 having integrally moulded therewith an extending lateral skirt 2 which is adapted to mate with the upper surface of the casing of a unit containing the pressure transducer and associated evaluation electronics. Depending from skirt 2 are two integral tabs 3 which may mate and latch with corresponding formations on the aforesaid casing.

The central substantially tubular passage is divided into two the presence of a perforate integral wall 5, i.e., a mesh. As can clearly be seen in FIG. 2, wall 5 is pierced by a plurality of cylindrical passages forming an array and including six cylindrical passages of slightly smaller dimensions than the rest in order to fill the entire cross-section efficiently. The array as shown in FIG. 2 is a particularly preferred embodiment of the present invention. We have found that this design provides a flow profile which is consistently turbulent across the range of expiratory flow for which the unit is designed.

In the wall of body 1 are two small apertures, one denoted 8 upstream of the wall 5 and the other denoted 9 downstream of it. On the outside of the main passage, these apertures are each surrounded by a cylindrical skirt 12 and 13 respectively. These skirts 12 and 13 are dimensioned with slightly tapered walls to mate and seal with corresponding formation on the casing of the main unit containing the pressure transducers and associated electronics. When the unit shown in FIGS. 1 and 2 is fitted to the casing, each of ports 8 and 9 is in respective communication with a pressure transducer located within the main equipment casing.

The left hand end of the unit as shown in FIG. 1 has a tapered exterior 15 over which may be fitted a suitable mouthpiece. The mouthpiece may be of conventional type and may if desired incorporate a non return valve enabling exhaled air to be blown through the flowhead shown in FIG. 1 from left to right, but not sucked back from right to left.

The flowhead may incorporate a low resistance hydrophilic filter to cover port 8. This has two advantages: first ther is a major reduction in the ease with which e.g. airborne moisture droplets could pass through port 8 and into the passage leading from the exterior of the main equipment casing to the pressure transducer and thereby prevent the water droplets finding their way into the transducer and thereby preventing proper operation. Secondly, the provision of such filter material serves to damp high frequency pressure oscillations which can arise within the main tube, thus reducing the possibility of any damage to the transducer. A second filter may be placed over port 9 for similar purposes.

In use, when exhaled breath is blown through the unit from left to right as shown in FIG. 1, because of the presence of the wall 5 which constitutes a constriction or resistance to the flow, the pressure upstream of wall 5 at port 8 is greater than that downstream of it at port 9. This difference is detected by the pressure transducer and may be converted by using known algorithms to a corresponding expiratory flow rate and by integration of the signal to a one second volume of expired air. The electronics may naturally sample this flow rate during the course of an exhalation and be arranged to display the peak expiratory flow rate and/or $FEV_1$ (Forced Expiratory Volume at one second).

The flowhead in accordance with the invention is preferably manufactured as an integral moulding from a suitable plastics material. Various commercially available grades of polystyrene have proved suitable. Care needs to be taken, however, for efficient reliable and repeatable operation, to ensure that the moulding around the apertures in wall 5 and around the two ports 8 and 9 is clean and free of any flash. By careful mould design, the flowhead may be produced as a disposable item, thus obviating the need to clean and disinfect the flowhead after use by one patient and before use by the next.

I claim:

1. A flowhead for use in lung function monitoring apparatus consisting essentially of a molded body member; a substantially cylindrical main channel within the body member; a mesh integrally molded with the body member, said mesh extending across an entire cross-section of the channel and dividing the channel transversely into two sections; and axially spaced ports in a side wall of the body member which are in communication with the channel, with one port being located on each side of the mesh, and each port having an axis parallel to one another and transverse to a longitudinal axis of the channel; wherein each port is surrounded on an exterior surface of the body member by a cylindrical sealing collar, and wherein the mesh includes a plurality of narrow substantially cylindrical passages axially aligned with the longitudinal axis of the channel.

2. A flowhead of claim 1 further including a hydrophilic filter material covering each port.

* * * * *